United States Patent [19]

Bassett et al.

[11] 4,082,787

[45] Apr. 4, 1978

[54] METHYL ISOCYANATE PROCESS

[75] Inventors: Robert James Bassett, Hockessin; Walter John Cordes; Julius Jakob Fuchs, both of Wilmington, all of Del.

[73] Assignee: E. I. Du Pont de Nemours and Company, Wilmington, Del.

[21] Appl. No.: 756,554

[22] Filed: Jan. 3, 1977

[51] Int. Cl.$^2$ ............................................. C07C 118/00
[52] U.S. Cl. ........................... 260/453 P; 260/453 PH
[58] Field of Search ...................... 260/453 P, 453 PH

[56] References Cited

U.S. PATENT DOCUMENTS 3,388,145  6/1968  Merz ................................. 260/453 P
3,969,389  7/1976  Urbach et al. ..................... 260/453 P Primary Examiner—Dolph H. Torrence

[57] ABSTRACT

Process for making methyl isocyanate comprising thermally dehydrochlorinating a solution of methyl carbamyl chloride in an aprotic nonpolar solvent, condensing the gases thereby formed at a temperature above the boiling point of methyl isocyanate so as to liquify at least part of said gases which are condensable at said temperature, removing HCl gas by condensing the remaining condensable gases at a temperature below the boiling point of methyl isocyanate, and separating methyl isocyanate from the condensate obtained in said first condensation step.

24 Claims, 3 Drawing Figures

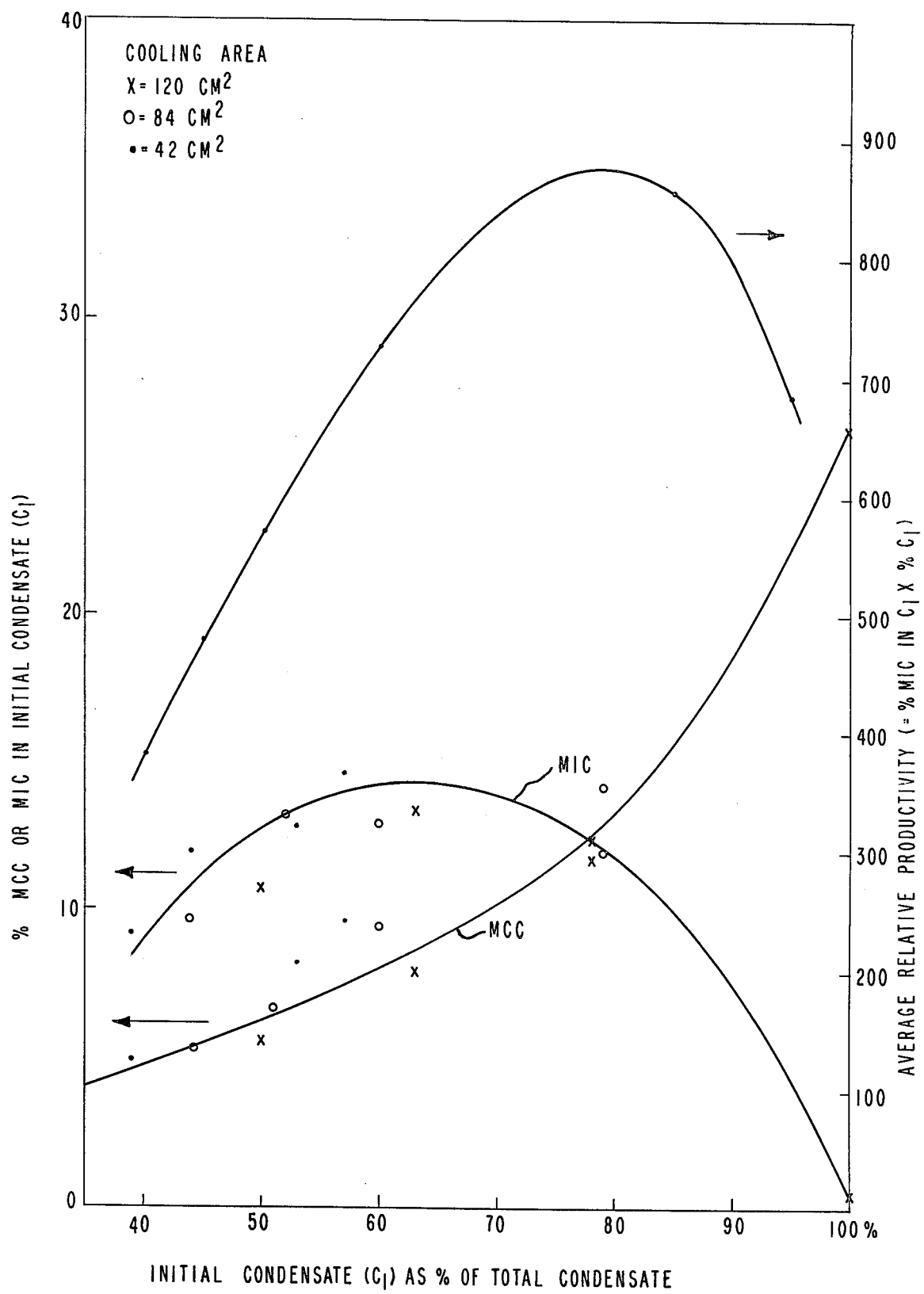

METHYL ISOCYANATE PROCESS

BRIEF SUMMARY OF THE INVENTION

In accordance with this invention, there is provided a novel process for manufacturing methyl isocyanate in high yields. In the process of this invention, a solution of methyl carbamyl chloride in an aprotic non-polar solvent is thermally dehydrochlorinated at a temperature above the boiling point of methyl carbamyl chloride; the gases formed thereby are initially condensed at a temperature above the boiling point of methyl isocyanate, so as to liquify at least part of the gases which are condensable at said temperature and thereby provide a condensate consisting essentially of a solution of methyl isocyanate and methyl carbamyl chloride in said solvent (enriched in methyl isocyanate); HCl is removed from the remaining condensable gases by condensing them at a temperature below that at which said initial condensation was performed; and methyl isocyanate is separated from the condensate obtained in said initial condensation step.

BACKGROUND OF THE INVENTION

Methyl isocyanate can be synthesized by reacting monomethylamine and phosgene at 240° to 250° C in a continuous vapor phase tubular reactor:

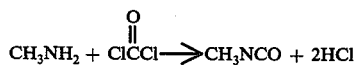
(a)

Methyl isocyanate and HCl react in an equilibrium reaction (b) to form methyl carbamyl chloride:

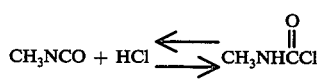
(b)

In equilibrium reaction (b), dissociation (dehydrochlorination) of methyl carbamyl chloride to methyl isocyanate and HCl approaches 100% at 240° C, but is almost negligible at 45° C. Thus, when the gases leaving the continuous hot tube reactor of synthesis reaction (a) are scrubbed in a packed column with refluxing solvent (e.g., chloroform or toluene) or refluxing phosgene plus solvent, excess phosgene and one mole of HCl (of the two moles formed) can be removed overhead, and a liquid stream consisting mainly of methyl carbamyl chloride and solvent, with a small percentage of methyl isocyanate, can be drawn off from the bottom of the column.

The boiling point of methyl isocyanate is 39° C., whereas the melting point of methyl carbamyl chloride is about 45° C. (and its boiling point is 92° C.) The equilibrium in the aforesaid dissociation reaction is shifted strongly to the right (to reassociation) at 39°–45° C. Consequently, it is impossible to separate pure methyl isocyanate from pure methyl carbamyl chloride simply by condensing methyl isocyanate in the presence of HCl.

Merz, in U.S. Pat. No. 3,388,145, discloses thermally dihydrochlorinating a solution of methyl carbamyl chloride to produce a mixture of solvent, methyl carbamyl chloride, methyl isocyanate and HCl, and removing HCl from that mixture by reflux in a condenser which is connected directly to the dehydrochlorination reactor. The condenser is cooled to a temperature substantially below the boiling point of the isocyanate so that only HCl is removed from that mixture. Moreover, Merz requires that a fractionating column be connected directly to the reactor and that the fractionating column and the reflux condenser be operated simultaneously with one another.

Slocombe et al., in U.S. Pat. No. 2,480,088, disclose preparation of methyl isocyanate by dehydrochlorinating methyl carbamyl chloride in the presence of an HCl acceptor. Slocombe et al. also disclose thermally dehydrochlorinating other carbamyl chloride compounds in the absence of an HCl acceptor, but only where the isocyanate (e.g., phenyl isocyanate) possesses a boiling point higher than the decomposition temperature of the carbamyl chloride.

DETAILED DESCRIPTION OF THE INVENTION

This invention relates to a process for preparation of methyl isocyanate (MIC) by thermal dehydrochlorination of a solution of methyl carbamyl chloride (MCC) in an aprotic nonpolar solvent at a temperature above the boiling point of MCC:

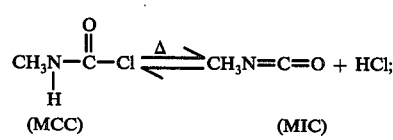

initially condensing the resultant reaction gases at a temperature above the boiling point of MIC so as to provide a liquid condensate containing MIC, MCC and said solvent wherein the ratio of MIC to MCC is greater than it is in said reaction solution; separating said liquid condensate from the gases remaining after said initial condensation; separating MIC from said condensate; and separating HCl from said remaining gases by condensing said remaining gases at a temperature below that at which said initial condensation step was performed. Because the liquid condensate resulting from the initial condensation step is richer in MIC than is the reaction solution, the gases remaining after the initial condensate step are richer in HCl than are the reaction gases. The enrichment of MIC in the initial condensate and the enrichment of HCl in the uncondensed gases promote more efficient conversion to and recovery of MIC as well as more effective removal of HCl.

The process of this invention comprising the use of an aprotic non-polar organic solvent and said initial condensation technique gives an unexpectedly efficient enrichment of MIC relative to MCC and solvent in the initial condensate. Separation of MIC from the initial condensate gives yields of MIC as high as 96% with surprisingly low loss of MCC as the result of bi- and tri-molecular condensation to trimethyl triazinetrione and related undesirable by-products such as allophanoyl chloride. This process is characterized by: a high temperature shift of the MCC ⇌ MIC + HCl equilibrium; an enriched MIC initial condensate stream; short vapor-condensate contact time in the initial condensation step; an organic solvent which reduces condensation side reactions of MCC; and efficient recovery of MIC from the enriched MIC condensate.

Figure 1:
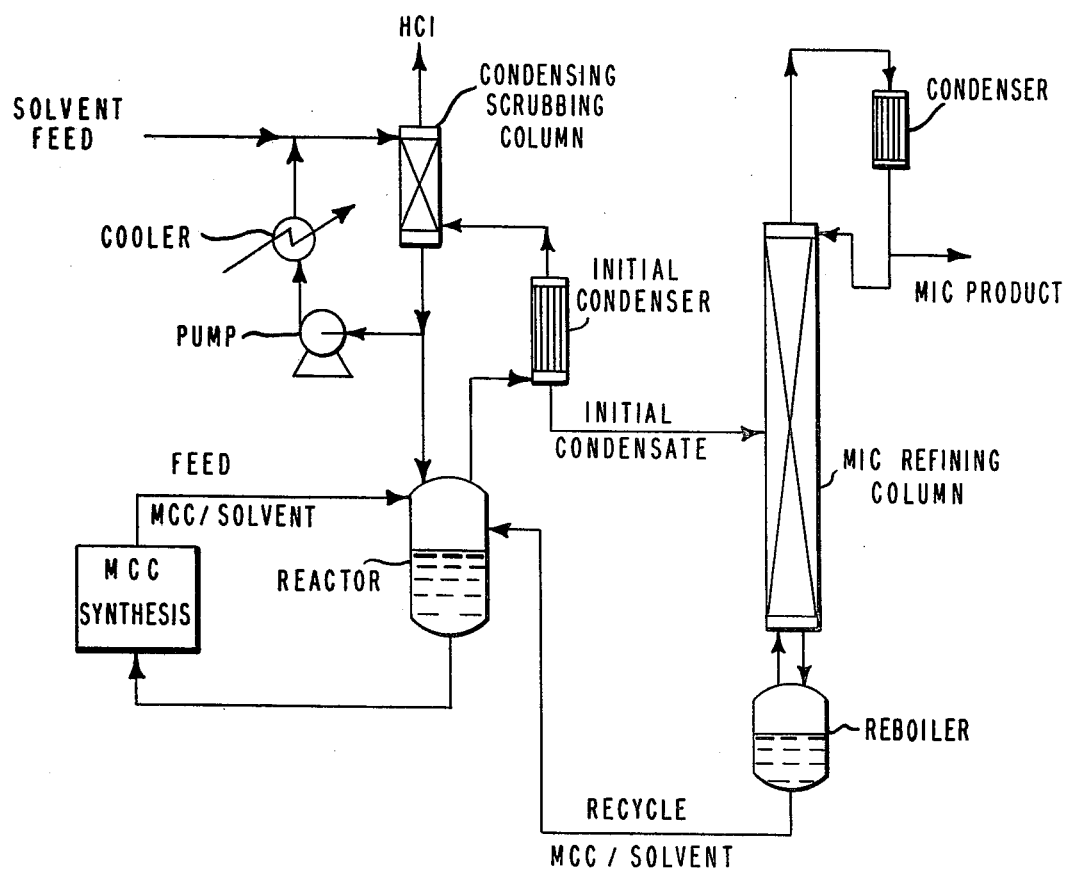

A schematic of an embodiment of the invention is outlined in FIG. 1. In a typical operation, (1) MCC and a non-polar aprotic organic solvent are fed to a reactor in which they are boiled at a temperature above the boiling point of MCC so as to dehydrochlorinate the MCC to MIC. Dehydrochlorination can be carried out at atmospheric pressure or pressures higher or lower than atmospheric. For economic reasons, atmospheric pressure is preferred. MCC feed concentrations to the reactor of 20-50% by weight in said solvent are preferred. Such concentrations can be obtained by feeding MCC and solvent separately to the reactor or a solution of MCC may be used. The MCC charge solution can contain MIC resulting from the preparation of the MCC, e.g. reaction of methyl amine with phosgene at about 240°-250° C. in the vapor phase, followed by quenching the resultant reaction gases in an aprotic nonpolar solvent at about 95° C. Solvents preferred for the dehydrochlorination process allow high temperature operation with minimum side reaction losses of MCC. Aromatic solvents such as monochlorobenzene, the isomeric dichlorobenzenes or toluene are preferred. Their high boiling points favor thermal dissociation of MCC and fractional distillation of MIC from solvent in the recovery step. The intrinsic properties of these solvents minimize bi- and tri-molecular condensation side reactions. (2) The dehydrochlorination reaction gases are then fed to a condenser in which they are cooled to a temperature above the boiling point of MIC and below the boiling point of the solvent so as to provide an initial liquid condensate stream in which the ratio of MIC:MCC is greater than it is in the reaction solution. The exact physical-chemical processes responsible for this favorable result are not well understood. The simultaneous processes of dissociation and recombination, condensation, and HCl diffusion from the gas to the liquid condensate phase interact in a complex way. Their effect on the enrichment of MIC in the initial condensate is not predictable by ordinary chemical engineering methods. The condenser used for the initial condensation step may be upflow or downflow, horizontal or vertical and can be of varying length to diameter. (3) The liquid condensate from the initial condensation step is charged to a MIC refining column. MIC is removed overhead as a gas and then condensed to a liquid in a condenser. A portion of the liquid MIC therefrom is returned to the top of the MIC refining column for reflux, and another portion is drawn off as the desired product. Refluxing MIC in the upper section of the column reacts with any HCl tending to pass up through the column so as to reform MCC. The resulting MCC which is high boiling relative to MIC is only slightly dissociated at the boiling point of MIC and is forced down the fractionating column. The still bottoms from the column, enriched in MCC, are returned to the reactor from the reboiler. (4) The gases from the initial condenser are removed overhead and HCl is removed therefrom in a condensing-scrubbing column.

In a preferred embodiment of this invention, toluene containing about 35% to 45% by weight of MCC is charged to the reactor. The solution is heated to and maintained at a temperature in the range between 95° and 105° C. at atmospheric pressure so as to dehydrochlorinate the MCC. The reaction gases are cooled in the initial condenser to the extent necessary that from about 25% to about 95% by volume thereof (usually at least 50% and preferably 75% to 90%) are condensed, and the liquid thereby formed has an exit temperature in the range between 50° C and 70° C.; preferably 55°-65° C. The vapors taken overhead from the partial condenser will, as a consequence, have an exit temperature in the range between 60° and 90° C., preferably 70°-80° C., most preferably 75°-80° C. The liquid condensate from the partial condenser, which contains 1.5 to 15% of MIC by weight in a toluene/MIC/MCC solution (preferably 10% to 12%) is fed to the MIC refining column. Product MIC is removed overhead and the still bottoms, which contain solvent and MCC, are returned to the reactor. When other solvents are used in this process, conditions will be selected to give similar performance.

In the following illustrative examples, percentages are by weight and densities were measured at 25° C. Although the examples and other portions of the specification relate particularly to a continuous process using toluene as the solvent and particularly identified equipment, the process can be run on a batch basis or with other solvents or equipment so long as they fulfill the functions and have the characteristics described herein.

EXAMPLE 1

The reactor and reboiler were filled to a certain level with toluene and brought to a boil. Then, a 40.36% solution of MCC in toluene was gradually added to the reactor until the temperature therein had decreased to 103° C., where it was maintained by continuously adding additional 40.36% MCC solution. The cooling area of the initial condenser was adjusted to give an exit gas temperature of 75° C., the gases being then further cooled in a water condenser plus a Dry-Ice condenser in a series (in place of the condensing-scrubbing column), the condensate of which was returned to the reactor. The HCl off-gas from the Dry-Ice condenser was absorbed in $H_2O$ and the acidity periodically titrated with standardized NaOH solution. The liquid condensate from the initial condenser with a temperature of at least 55° C was continuously fed to the middle of the MIC refining column, from which essentially pure MIC was isolated. The liquid level in the reboiler was held constant by continuously recycling liquid, with a temperature of 104.5° C, back to the reactor, where the liquid level was being held constant by continuously drawing off a purge stream of solution.

During a 3-hour period of continuous operation, the following data were obtained:

MCC feed to the reactor:
    502 ml of 40.36% MCC solution ($d = 0.9847$) = 2.133 moles MCC Purge Stream out of the reactor:
    216.9 g in 3 hours;
    1.56% MCC = 0.036 moles
    1.07% MIC = 0.052 moles Initial Condensate (to MIC refining column):
    $d = 0.8734$; 2.21% MCC; 7.17% MIC
    Flow: 21.5 ml/min = 3380 g in 3 hours Condensate from second condensing system (to the reactor):
    46.7% MCC, 0% MIC, balance: toluene saturated with HCl
    Flow: 4.0 ml/min = 720 g in 3 hours Recycle Stream (from the reboiler to the reactor):
    $d = 0.8673$; 2.68% MCC; 0.79% MIC HCl absorbed in $H_2O$:
    2.045 moles in 3 hours MIC isolated by distillation:
    113.5 g; 96.22% MIC = 1.914 moles Yield:

$$\frac{\text{moles MIC formed}}{\text{moles HCl formed}} = \frac{1.914 + .052}{2.045} \times 100 = 96.1\%$$

EXAMPLE 2

Example 1 was repeated with the exception that the reactor temperature was maintained during the continuous operation at 97.0° C. This, in turn, caused the reboiler temperature to stabilize at 96.5° C.

In the course of a 3-hour continuous operation, the following data were obtained:
MCC feed to the reactor:
 785 ml of 36.54% MCC and 2.42% MIC solution in toluene; $d = 0.9769 = 2.996$ moles MCC and 0.325 moles MIC
Purge stream out of the reactor:
 420.4 g in 3 hours;
 4.65% MCC = 0.209 moles
 2.11% MIC = 0.155 moles
Initial Condensate (to MIC refining column):
 $d = 0.8978$; 9.21% MCC; 11.42% MIC
 Flow: 25.0 ml/min = 4040 g in 3 hours
Condensate from second condensing system (to the reactor) 65.7% MCC, 0% MIC, balance: toluene saturated with HCl
 Flow: 2.75 ml/min = 495 g in 3 hours
Recycle stream (from the reboiler to the reactor):
 10.78% MCC; 2.07% MIC
HCl absorbed in H$_2$O:
 2.627 moles in 3 hours
MIC isolated by distillation:
 166.4 g; 95.75% MIC = 2.793 moles
Yield:

$$\frac{\text{moles MIC formed}}{\text{moles HCl formed}} = \frac{2.793 + .155 - .325}{2.627} \times 100 = 99.8\%$$

EXAMPLE 3

Figure 2:
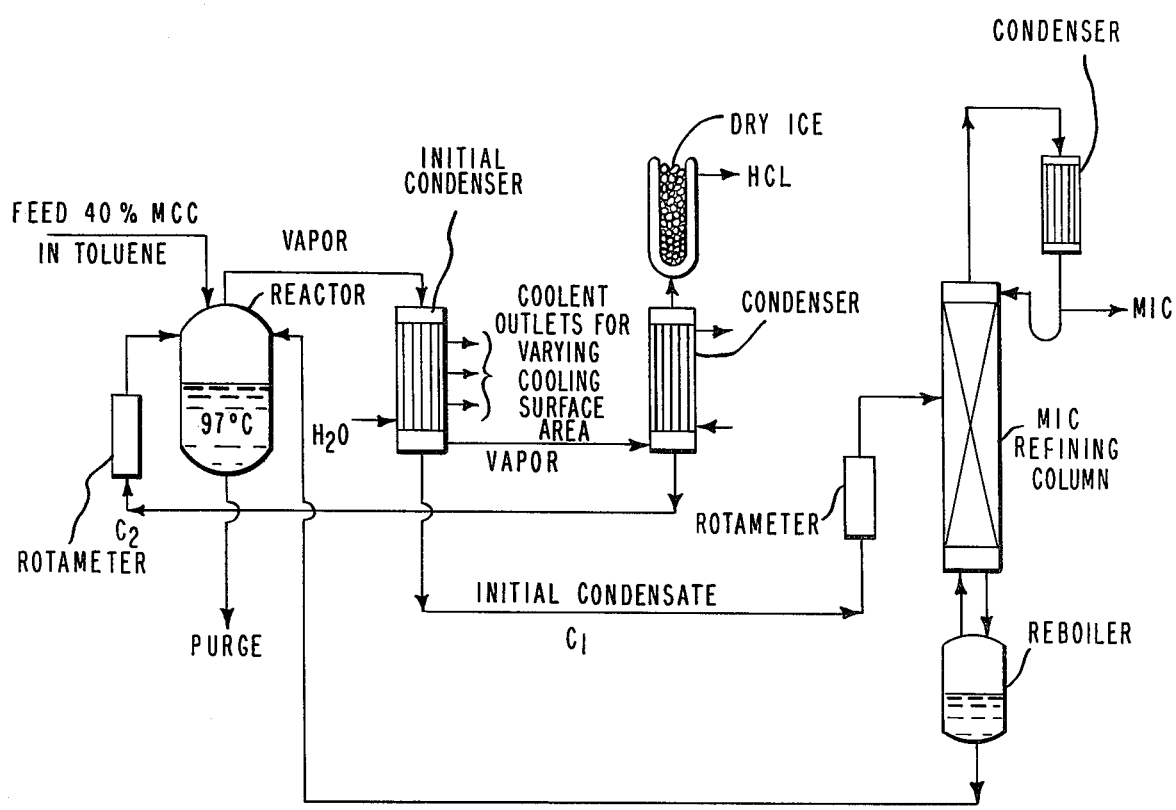

The equipment shown in the attached FIG. 2 was used to determine how the cooling water temperature to the initial condenser and the cooling area of the initial condenser affect the amount of the initial condensate, its temperature and composition when a 40% MCC solution in toluene was used to maintain the reactor temperature at 97° C. The process conditions and results are summarized in Table I. The results are also shown graphically in FIG. 3 wherein the composition of the initial condensate ($C_1$) and the average relative productivity (% MIC in $C_1$ × % $C_1$) are plotted vs. the amount of initial condensate expressed as a percentage of the average total flow in these experiments.

TABLE I

| Run No. | Cooling water to Initial Condenser (°C) | Cooling area (cm$^2$) in Initial Condenser | Vapor temp. to Initial Condenser (°C) | Liquid temp.from Initial Condenser (°C) | Vapor temp.from Initial Condenser (°C) | Flow ml/min $C_1$ | Flow ml/min $C_2$ | Total Flow $C_1 + C_2$ ml/min | Flow $C_1$ as % of Avg. Tot. Flow |
|---|---|---|---|---|---|---|---|---|---|
| 1 | 0 | 42 | 90 | 60.0 | 76.5 | 10.8 | 8.1 | 57 | |
| 2 | 0 | 84 | 90 | 58.5 | 76.0 | 14.9 | 4.1 | 19.0 | 79 |
| 3 | 0 | 120 | 90 | 60.0 | 70.0 | 19.7 | 0 | 19.7 | 100 |
| 4 | 24.3 | 42 | 90 | 60.0 | 77.5 | 10.0 | 10.2 | 20.2 | 53 |
| 5 | 24.3 | 84 | 90 | 59.0 | 76.0 | 11.4 | 7.1 | 18.5 | 60 |
| 6 | 24.3 | 120 | 90 | 58.0 | 76.0 | 14.8 | 4.1 | 18.9 | 78 |
| 7 | 35.0 | 42 | 90 | 62.0 | 79.0 | 8.4 | 10.2 | 18.6 | 44 |
| 8 | 35.0 | 84 | 90 | 59.0 | 77.0 | 9.8 | 8.6 | 18.4 | 52 |
| 9 | 35.0 | 120 | 90 | 58.0 | 76.0 | 11.9 | 7.25 | 19.15 | 63 |
| 10 | 50.0 | 42 | 90 | 65.0 | 80.0 | 7.4 | 11.0 | 18.4 | 39 |
| 11 | 50.0 | 84 | 90 | 64.0 | 77.0 | 8.4 | 10.3 | 18.7 | 44 |
| 12 | 50.0 | 120 | 90 | 62.0 | 76.0 | 9.4 | 9.5 | 18.9 | 50 |

Average Total Flow: 18.9

| Run No. | Density $C_1$ gr/ml | $C_1$ Composition %MCC | $C_1$ Composition % MIC | $C_2$ Composition % MCC | $C_2$ Composition % MIC | Vapor Residence Time (Avg) $\bar{\tau}_v$ (sec.) | Vapor Residence Time (inlet Condition) $\tau_{vo}$ (sec.) | Liquid Residence Time $\tau L$ (sec.) |
|---|---|---|---|---|---|---|---|---|
| 1 | .9047 | 9.65 | 12.29 | 48.3 | 0.29 | 0.19 | 0.14 | 2.4 |
| 2 | .9172 | 14.20 | 11.03 | 50.0 | 0 | 0.34 | 0.24 | 3.2 |
| 3 | .9505 | 26.28 | 5.29 | — | — | 0.50 | 0.35 | 3.5 |
| 4 | .8975 | 8.20 | 11.43 | 44.6 | 2.62 | 0.19 | 0.14 | 2.6 |
| 5 | .9022 | 9.49 | 11.50 | 51.3 | 0 | 0.34 | 0.24 | 4.2 |
| 6 | .9098 | 1.90 | 11.21 | 60.0 | 0 | 0.50 | 0.35 | 4.7 |
| 7 | .889 | 5.38 | 11.00 | 41.7 | 3.97 | 0.19 | 0.14 | 3.2 |
| 8 | .8940 | 6.79 | 11.65 | 50.6 | 0.41 | 0.34 | 0.24 | 4.8 |
| 9 | .8975 | 8.05 | 11.71 | 57.0 | 0 | 0.50 | 0.35 | 5.8 |
| 10 | .8875 | 4.89 | 9.64 | 40.3 | 6.78 | 0.19 | 0.14 | 3.6 |
| 11 | .8886 | 5.53 | 9.87 | 46.9 | 3.99 | 0.34 | 0.24 | 5.5 |
| 12 | .8894 | 5.74 | 10.39 | 51.8 | 2.85 | 0.50 | 0.35 | 7.4 |

Note: $\bar{\tau}_v = \dfrac{\text{free volume in condenser}}{\text{average vapor flow rate in condenser}}$ $\tau_{vo} = \dfrac{\text{free volume in condenser}}{\text{inlet vapor flow rate}}$

What is claimed is:

1. A process for making methyl isocyanate comprising thermally dehydrochlorinating a solution of methyl carbamyl chloride in an aprotic non-polar solvent at a temperature above the boiling point of methyl carbamyl chloride; initially condensing the reaction gases thereby formed at a temperature above the boiling point of methyl isocyanate so as to liquify at least part of the gases which are condensable at said temperature and thereby provide an initial liquid condensate consisting essentially of a solution of methyl isocyanate and methyl carbamyl chloride in said solvent wherein the ratio of methyl isocyanate to methyl carbamyl chloride is greater than it is in said reaction solution; separating said initial liquid condensate from the gases remaining after said initial condensation; separating methyl isocyanate from said initial condensate; and separating HCl from said remaining gases.

2. The process of claim 1 wherein methyl carbamyl chloride constitutes between 20% and 50% by weight of said solution.

3. The process of claim 2 wherein said solvent minimizes side reactions and has a boiling point sufficiently high so as to favor thermal dissociation of methyl carbamyl chloride and fractionation of methyl isocyanate therefrom.

4. The process of claim 3 wherein from about 25% to about 95% by volume of said condensable gases are liquified in said initial condensation step.

5. The process of claim 4 wherein said solvent is toluene.

6. The process of claim 5 wherein methyl carbamyl chloride constitutes between about 35% and 45% by weight of said solution.

7. The process of claim 6 wherein said thermal dehydrochlorination step is performed at temperatures between 95° and 105° C.

8. The process of claim 7 wherein said initial condensate has an exit temperature in the range between 50° and 70° C.

9. The process of claim 8 wherein said solution of methyl carbamyl chloride is continuously dehydrochlorinated and methyl isocyanate is continuously recovered therefrom.

10. The process of claim 9 wherein said initial condensate has an exit temperature in the range between 55° and 65° C.

11. The process of claim 4 wherein at least 50% by volume of said condensable gases are liquified.

12. The process of claim 11 wherein said solvent is toluene.

13. The process of claim 12 wherein methyl carbamyl chloride constitutes between about 35% and 45% by weight of said solution.

14. The process of claim 13 wherein said thermal dehydrochlorination step is performed at temperatures between 95° and 105° C.

15. The process of claim 14 wherein said initial condensate has an exit temperature in the range between 50° and 70° C.

16. The process of claim 15 wherein said solution of methyl carbamyl chloride is continuously dehydrochlorinated and methyl isocyanate is continuously recovered therefrom.

17. The process of claim 16 wherein said initial condensate has an exit temperature in the range between 55° and 65° C.

18. The process of claim 11 wherein 75% to 90% by volume of said condensable gases are liquified.

19. The process of claim 18 wherein said solvent is toluene.

20. The process of claim 19 wherein methyl carbamyl chloride constitutes between 35% and 45% by weight of said solution.

21. The process of claim 20 wherein said thermal dehydrochlorination step is performed at temperatures at between 95° and 105° C.

22. The process of claim 20 wherein said initial condensate has an exit temperature in the range between 50° and 70° C.

23. The process of claim 22 wherein said solution of methyl carbamyl chloride is continuously dehydrochlorinated and methyl isocyanate is continuously recovered therefrom.

24. The process of claim 23 wherein said initial condensate has an exit temperature in the range between 55° and 65° C.

* * * * *

Disclaimer 4,082,787.—*Robert James Bassett*, Hockessin; *Walter John Cordes*, Wilmington, and *Julius Jakob Fuchs*, Wilmington, Del. METHYL ISOCYANATE PROCESS. Patent dated Apr. 4, 1978. Disclaimer filed May 5, 1980, by the assignee, *E. I. Du Pont de Nemours and Company*.

Hereby enters this disclaimer to claims 1, 2, 3, 4, 11 and 18 of said patent.

[*Official Gazette June 24, 1980.*]